United States Patent [19]

Adam et al.

[11] 3,976,544

[45] Aug. 24, 1976

[54] WATER-SOLUBLE IMMUNOLOGICAL ADJUVANTS, IN PARTICULAR FOR VACCINES, OBTAINED FROM MYCOBACTERIA AND RELATED MICROORGANISMS AND PROCESS FOR THEIR EXTRACTION

[75] Inventors: Arlette Adam, Palaiseau, France; Frank Berger, Princeton, N.J.; Louis Chedid, Paris, France; Edgar Lederer, Sceaux, France; Jean-Francois Petit, Paris, France,; Rita Ciorbaru, Montrouge, France

[73] Assignee: The Agence Nationale de Valorisation de le Recherche, Paris, France

[22] Filed: June 19, 1973

[21] Appl. No.: 371,512

[52] U.S. Cl. .................................... 195/2; 195/4; 195/96; 424/92
[51] Int. Cl.² ................... A61K 27/00; C12D 13/02
[58] Field of Search ............... 195/96, 2, 4; 424/88, 424/92, 93, 195; 260/236.5

[56] References Cited
UNITED STATES PATENTS

| 3,529,057 | 9/1970 | Tsuchiya et al. ..................... 424/92 |
| 3,876,779 | 4/1975 | Adam et al. ......................... 195/2 X |

OTHER PUBLICATIONS

Chem. Abstracts, 73:12587s.
Chem. Abstracts, 68:10391w.
Chem. Abstracts, 77:P118187j.
Chem. Abstracts, 66:45009p.
Chemical Abstracts, 71:45901b, (1969).
Chemical Abstracts, 71:99074c, (1969).
White, "Adjuvants in Production of Delayed Hypersensitivity," *British Medical Bulletin,* vol, 23, No. 1, pp. 39–45, (1967).

*Primary Examiner*—Alvin E. Tanenholtz
*Assistant Examiner*—Thomas G. Wiseman

[57] ABSTRACT

The invention pertains to a water-soluble immunological adjuvant, especially for vaccines. It is obtained by enzymatic treatment of mycobacteria or Nocardia whole cells in aqueous medium and by a recovery from said aqueous medium.

14 Claims, No Drawings

WATER-SOLUBLE IMMUNOLOGICAL ADJUVANTS, IN PARTICULAR FOR VACCINES, OBTAINED FROM MYCOBACTERIA AND RELATED MICROORGANISMS AND PROCESS FOR THEIR EXTRACTION

The present invention relates to soluble agents which are efficient immunological adjuvants for stimulating in a host immunitary responses to various types of antigens. More specifically, the invention is concerned with adjuvants adapted to reinforce and enhance the activity of weak immunogens.

This invention relates more particularly to soluble agents which are effective adjuvants usable for immunization of men and warm-blooded animals against bacterial, viral and parasitary infections and against various tissular antigens of normal or pathologic origin, in particular against tumors.

In copending patent application SN 307,614 filed 20 Nov. 17, 1972, there have been described soluble agents of this type, extracted from mycobacteria or Nocardia cells, said agents containing oligomers or portions thereof, the monomer units of said oligomers having a chemical structure similar to that of the monomer units of micro-organism cell-walls from which they are originated, except that the lipidic portion is very small or inexistent.

There has also been described in the main patent application a process for preparing such agents, which process essentially comprises cultivating a strain of mycobacteria or Nocardia cells, collecting cells of the cultivating strain, causing the rupture thereof, recovering ruptured cell walls, e.g. by differential centrifugation, separating and removing waxes, free lipids, proteins and nucleic acids, causing digestion of delipidated material from cell walls by means of a murolytic enzyme, such as lysozyme, eliminating the solid residue and collecting the aqueous fraction containing said soluble agents.

While the aqueous fraction, which contains the agent under consideration in crude state, has itself highly useful adjuvant properties, it is preferred to effect an additional purification of the agent by subjecting the aqueous fraction to a filtering through a molecular sieve; for example through a gel column of polydextran or similar material, e.g. the gel known under trademark "Séphadex G75" or "Séphadex G50".

This method has nevertheless a number of drawbacks, concerning the difficulty of preparing purified walls in substantial amounts, the need of effecting cell-rupturing operations and the separation of ruptured wall, in particular by differential centrifugations, which operations are both difficult to perform and time-consuming, and finally the low yields which can be obtained (a maximum of 1% by weight with respect to initial dry bacillus).

The present invention aims to overcome these drawbacks and to provide, in particular, a simplified process which enables adjuvant agents of the type disclosed in the copending application to be prepared from the same micro-organisms in substantially higher yields.

The invention also aims to provide a process for obtaining a soluble adjuvant agent having a high degree of purity.

The process of the present invention, which comprises cultivating a strain of mycobacteria or Nocardia cells, recovering cells from the cultivated strain, and treating them with delipidating solvents is characterized in that the delipidated whole cells are subjected to the action of a murolytic enzyme, such as a muramidase, e.g. lysozyme, the solid fraction being thereafter removed and the aqueous fraction which contains the adjuvant agents recovered.

The delipidating step is advantageously effected under reflux in an extractor of the type Soxhlet of Kumagawa, the delipidated cells being afterwards washed with water, then with a 0.1 M ammonium acetate buffer at pH 6.2, before being subjected to the action of lysozyme. This buffer which enables lysozyme to act under optimum conditions, may be subsequently eliminated in totality, e.g. by lyophilisation.

The adjuvant agent contained in the aqueous fraction may be advantageously subjected to a further purifying treatment, such treatment comprising, for example, a lyophilisation of the aqueous fraction, the taking up of the dry extract in an aqueous solution of the type permitting a filtering on a molecular sieve, especially in 0.1 M acetic acid. Advantageously, the molecular sieves used are of the same type as disclosed in the copending application, such as the products sold under the trademark "Séphadex", for instance "Séphadex G75" or "Séphadex G50".

As in the copending application, the process according to the invention may be applied to mycobacteria both pathogenic and non-pathogenic, to Nocardia cells and related micro-organisms. Among micro-bacteria which may be used as raw material for the preparation of adjuvants according to the invention, there may be mentioned: *Mycobacterium tuberculosis*, var. hominis or bovis, in particular Calmette Guerin bacillus (BCG), *Mycobacterium kansasii*, *Mycobacterium smegmatis*, or other organisms belonging to genus Mycobacterium.

The process according to the invention enables immunological adjuvant agents of the type disclosed in the main patent application to be obtained, said agents being characterised in that they contain:

a. neutral sugars (containing in particular galactose and arabinose);
b. amino-sugars (D-glucosamine and D-muramic acid);
c. amino-acids (including L- and D-alanines, D-glutamic acid and meso- $\alpha$ - $\epsilon$ - diamino-pimelic acid);
d. if desired, lipids in amounts lower or at most equal to 5 %.

These agents are stable at ordinary ambiant temperatures for at least several months and may be lyophilized without loss of activity. After lyophilization, the purified agents under consideration provide a snow-white flaked material, which is readily soluble in water and gives a slightly opalescent solution. These agents are insoluble in ether, chloroform, acetone and ethanol-chloroform mixtures.

The agents which are thus obtained contain an amount of amino-acids higher than those disclosed in the copending application. This fact can be possibly explained as follows: these agents contain a number of amino-acids other than those of peptidoglycane, which have not been extracted in the course of the aforesaid treatments.

According to an additional feature of the invention, the agents obtained can be, if desired subjected to an additional purification step, for removing at least partially the last mentioned amino-acids, said step comprising incubating the agents with a proteolytic enzyme, such as trypsin, in an aqueous medium, for example in a buffer solution of a pH from around 7.5 to around 8.2.

Further objects and features of the invention will be developed in the following description of preferred embodiments concerning the cultivation and the extraction of agents in accordance with the invention, it being understood that this description is given merely by way of examples without limiting the scope of the invention as defined by the appended claims.

EXAMPLE 1

Preparation of fractions containing the adjuvant agent from whole cells of *M. smegmatis*.

Bacilla of *Mycobacterium smegmatis*, a strain of which has been deposited at "American Type Culture Collection" under the number ATCC NBR 21732, are cultivated for nine days at 37°C in a Roux plate on Sauton medium; they are recovered by filtering and washed several times with distilled water. Thereafter they are placed in the cartridge of a Soxhlet extractor and are extracted successively at reflux with acetone, ethyl alcohol, chloroform and chloroform-methanol mixture (87:13), thereafter dried with ether, then washed by suspending them in 100 times their weight of water and centrifuged. This washing is repeated twice more with water, then twice with 0.1 M ammonium acetate at pH 6.2. Finally, bacilla are resuspended in 100 times their initial weight of said buffer; the suspension has added thereto lysozyme (1% by weight of delipidated bacilla). After 18 hours of incubation at 37°C in the presence of a few drops of toluene, in order to prevent bacteria to be contaminated, the suspension is filtered. Bacilla are resuspended in ammonium acetate and are subjected to reincubation in the presence of lysozyme under the same conditions as previously. The filtrates from both incubations are combined and lyophilized.

This lyophilisate thereafter called "crude substance C", possesses an adjuvant activity while being substantially free of serious secondary effects as will be seen in a further part of the specification.

The composition of "crude substance C" is as follows:

| | |
|---|---|
| neutral sugars: | 45% (arabinose and galactose) |
| amino-sugars: | 16% (glucosamine and muramic acid after hydrolysis) |
| amino-acids: | 29% (of which 17% are comprised of alanine (Ala), glutamic acid (Glu) and meso α-ε-diaminopimelic acid (DAP) |
| phosphorus: | 0.9% |
| lipids: | less than 5% |

This lyophilisate has also been subjected to a further purification by dissolving in 0.1 M acetic acid and filtering on a "Sephadex G 75" column (height = 80 cm; diameter = 2.5).

The first-peak substance coming out from the column, called thereafter "Substance C" has the following composition:

| | |
|---|---|
| neutral sugars: | 75% (arabinose and galactose) |
| amino-sugars: | 10–12% (glucosamine and muramic acid after hydrolysis) |
| amino-acids: | 15% (12% comprised of: Ala, Glu, DAP) |
| lipids: | less than 5% | its sedimentation coefficient in a phosphate buffer, pH 7.0: $\mu = 0.1$, at 20°C and at a concentration $C = 4.8$ mg/ml is about $S_{20} = 1.95$.

It is shown by ultracentrifugation that "Substance C" is only slightly polydispersed.

It will be noted that 100 mg of "Substance C" are obtained from 2 g of delipidated bacilla, which corresponds to a yield nearly ten fold of that obtained by the process described in the main patent application.

Finally, it will be seen that the fraction corresponding to the second elution peak also contains meso-α-ε-diaminopimelic acid and amino-sugars, as the fraction (Substance B) disclosed in the main patent application, corresponding to the second elution peak obtained in the course of the last purification step of the method described in this application and applied to the same original micro-organisms.

EXAMPLE 2

Other purified fractions containing an adjuvant agent from other loads of *M. segmatis* whole cells have been obtained under conditions substantially identical to those described above, except for the delipidating step which has been effected by successive extractions with:

1. denaturated absolute alcohol, in order to achieve a first deshydration of the cells; and thereafter in a Soxhlet extractor with
2. denaturated absolute alcohol
3. chloroform
4. chloroform-methanol mixture (87 : 13);
5. petroleum ether (boiling in the range 96°–110°C).

The fractions obtained (first peaks) after purification on "Sephadex" gel are called thereafter "substance C1" and "substance C2".

EXAMPLE 3

Preparation of a fraction containing an adjuvant agent from whole cells of *Nocardia opaca* (ATCC No. 21953).

This organism is cultivated under medium aeration during 46 hours at 30°C in a fermentor on the following medium:

| | |
|---|---|
| Meat extract | 0.4% |
| Yeast | 0.2% |
| "Bactopeptone Difco" | 2% |
| Na Cl | 0.5% |
| pH 7.2 | |

The cells are dried with acetone, then placed in a Soxhlet extractor and delipidated at reflux with acetone, ether, chloroform, ethyl alcohol and a chloroform-methanol mixture (87:13). These cells are thereafter dried with acetone, resuspended in 100 times their weight of water, centrifuged, washed again in water and twice in an ammonium acetate buffer 0.1 M at pH 6.2. Finally, the cells are resuspended in 100 times their weight of ammonium acetate buffer and incubated with lysozyme (1% by weight of delipidated bacilla) during 18 hours at 37°C in the presence of a few drops of toluene. The cells are thereafter separated by filtering on sintered glass n° 4 and reincubated in the same conditions as before. The filtrates from both incubations are combined and lyophilized.

The lyophilisate, call thereafter "crude substance D", has the following composition:

| | |
|---|---|
| Neutral sugars: | 20–28% (among which galactose, |

-continued

| | |
|---|---|
| | glucose, arabinose and mannose) |
| Amino-sugars: | 8.8% (glucosamine and muramic acid after hydrolysis) |
| Amino-acids: | 40–44% (of which 15% comprised of: Ala, Glu, DAP) |
| Lipids: | 5–7% |
| Phosphorus: | about 5% |

The yield of "crude substance D" is 300 mg per 15 g of delipidated bacilla.

Filtration of a solution in 0.1 N acetic acid of "crude substance D" on a column of "Sephadex G75" having a height of 80 cm and a diameter of 2.5 cm, provides three elution "peaks", the fractions corresponding to each of said peaks having the following compositions:

| | |
|---|---|
| First peak: | |
| Neutral sugars: | 42% (glucose, galactose, ribose, traces of mannose and arabinose). |
| Amino-sugars: | 1–2% (glucosamine and muramic acid after hydrolysis) |
| Amino-acids: | 40% |
| Lipids: | less than 5% |
| Phosphorus: | about 2% |
| No DAP | |
| Second peak: | |
| Neutral sugars: | 16% (the same as in crude substance D but in different proportions) |
| Amino-sugars: | 18–19% (glucosamine and muramic acid after hydrolysis) |
| Amino-acids: | 39% (of which 20% are comprised of Ala, Glu, DAP) |
| Lipids: | about 5% |
| Phosphorus: | about 2% |
| Third peak: | |
| Neutral sugars: | 12% (among which glucose, galactose, ribose) |
| Amino-sugars: | 14% (glucosamine and muramic acid after hydrolysis) |
| Amino-acids: | 19% (Ala, Glu and DAP: 11%) |
| Lipids: | less than 5% |
| Phosphorus: | 5% |

Said fractions, obtained from 300 mg of "crude substance D", represent respectively 40 mg for the first peak, 120 mg for the second peak and 140 mg for the third peak.

The second and third peaks contain those components which are characteristic of the adjuvants of the invention. It is mainly the fraction corresponding to to the second peak, which is called thereafter "substance D", which has been subjected to the pharmacological tests disclosed hereafter.

EXAMPLE 4

Fifty mg of an adjuvant agent, extracted from *M. smegmatis*, prepared and purified as described in Example 1, are subjected to a supplementary purification operation, by incubation with 50 mg of insoluble trypsin manufactured by the company Boehringer (Germany), in 4 ml of a phosphate buffer 0.07 M pH 7.8 for 24 hours at 37°C, agitated by means of a magnet bar. The incubation mixture is then centrifuged, the supernatant filtered on a column of "SEPHADEX G75" (diameter = 2.5 cm, height = 80 cm) in acetic acid 0.1 N.

The first filtration peak contains 35 mg of highly purified agent (Substance E 1).

EXAMPLE 5

200 mg of an adjuvant agent, extracted from *M. smegmatis*, prepared and purified as described in Example 1, are subjected to a supplementary purification operation, by incubation with 1 mg of trypsin, manufactured by the company CHOAY S.A. (France), in 20 ml of phosphate buffer 0.07 M pH 7.8 for 18 hours at 37°C. The incubation mixture is then concentrated to 5 ml by lyophilisation, then filtered on a column of a filtration agent in water, the filtration agent being that commercialized under the name INDUBIOSE AcA 5/4 by the company styled "Industrie Biologique Francaise" (diameter = 2.5 cm, height = 80 cm).

The first filtration peak contains 150 mg of highly purified agent (Substance E2).

Results similar to those of Examples 4 and 5 are obtained by having recourse to other enzymes, such as pronase, chymotrypsin or subtilisin and/or other buffers enabling the establishment of a pH from 7.5 to 8.2, such as an ammonium carbonate buffer or a tris (hydroxymethyl) aminomethane.

Pharmalogical properties of the agents obtained

The substances which have been described possess pharmacological properties entirely similar to those of substances specifically disclosed in the copending application. Their high adjuvant activity, in the absence of the serious drawbacks of the prior art compositions such as the Freund complete adjuvant, makes said substances highly appropriate for both human and veterinary therapeutics.

The substances tested are those which have been identified in the Examples as: "Crude Substance C"; "Substance C"; "Substance C1"; "Substance C2"; "Substance D"; "Substance E1" and "Substance E2".

In the tests described below, the substances to be studied have often been suspended in a mineral oil or in a mineral oil-water emulsion. The oil used was a product sold under the trademark "Bayol F". The suspension was formed in the presence of a dispersing agent such as glycerol monooleate or the dispersing agent available under the trademark "Arlacel A". In some cases, the properties of the substances tested have been compared with those of whole mycobacteria or mycobacterial fractions, those of conventional Freund's complete adjuvant (FCA), those of the Freund's incomplete adjuvant (FIA), i.e. the Freund's adjuvant containing no bacteria.

A — Demonstration of adjuvant activity of the substances according to the invention 1. Adjuvant activity of the substances on the rate of Serum antibodies with respect to ovalbumin in guinea-pigs; quantitative precipitation and passive hemo-agglutination:

The substances which have been subjected to this test are "Crude Substance C"; "Substance C1","Substance C2" and "Substance D".

A soluble antigen, namely ovalbumin (5 mg), was added to each of the tested substances and the mixture obtained in each case added to incomplete Freund's adjuvant (FIA), then injected as an aqueous emulsion of "Bayol F" in the presence of the dispersing agent "Arlacel A" into the foot-pan of guinea-pigs. Each substance to be tested was administered to groups of 5 or 6 guinea-pigs of about 350 g body weight. The controls were injected with a mixture of ovalbumin with incomplete Freund's adjuvant (FIA) or complete Freund's adjuvant (FCA) the latter consisting of FIA and *M. butyricum* cells. The rates of anti-bodies with respect to ovalbumin were determined 21 days after injection. The induced antibody production was determined by quantitative precipitation in accordance with the method described by Gierer and Schramm (Zeit.

für Naturforsch., 1956, 116 : 138), and by passive hemoagglutination of erythrocytes coated with ovalbumin in the manner described by Stavitsky (J. Immunol., 1954, 72 : 360-368).

The serums were sampled 21 days after injection of the tested substances with antigin. In tables IA and IB hereafter are shown the mean values obtained in a series of tests and in each group of hemo-agglutinations, on the one hand, and serum quantitative precipitations, on the other hand. It can be deducted from the comparison of the results obtained in the control animals and the treated animals respectively, that tested substances stimulate very strongly the forming of antibodies. The results are expressed as reciprocals of serum dilution in the case of hemo-agglutination and in $\mu g$ of antigen-antibody complex per ml of serum in the case of quantitatine precipitatons.

TABLE I A

| Products injected and doses per guinea-pig | Hemagglutination | Precipitation ($\mu g$ AG/AC per ml of serum) |
|---|---|---|
| Controls FIA | 2,880 | 300 |
| "Raw Substance C": 200 $\mu g$ | 10,130 | 5,750 |

TABLE I B

| Products injected and doses per guinea-pig | Hemagglutination | Precipitation ($\mu g$ AG/AC per ml of serum) |
|---|---|---|
| Controls FIA | 840 | 616 |
| Controls FCA | 1,800 | 2,710 |
| "Substance C" 200 $\mu g$ | 3,300 | 5,020 |
| "Substance C" 200 $\mu g$ | 3,200 | 4,340 |
| "Substance C1" 200 $\mu g$ | 2,130 | 4,850 |
| "Substance C2" 200 $\mu g$ | 2,000 | 4,750 |

2. Adjuvant activity of the substances on the rate of elimination of antigen

The immunoadjuvant action of the abovementioned substances has been established by administering to mice by the intraperitoneal route, bovine albumine serum (BAS) used as antigen. In the following experiment, all of the mice have received 0.5 mg of BAS, with the exception of a control group. The other groups have received at the same time as the BAS, 50 $\mu g$ respectively of "Substance C", "Substance E1" and "Substance E2". In each case, the adjuvant agent had been mixed with antigen in saline solute.

Ten days later, these animals received by the intraperitoneal route, 5 $\mu g$ of radioactive BAS (marked with $^{125}$I). The next day, 50 $\mu l$ of blood were taken from each mouse and their radioactivity measured in a scintillation counter. The residual radioactivity is calculated according to the following formula:

$$\frac{\text{radioactivity recovered} \times K}{\text{radioactivity injected}} \times 100$$

in which K is a constant established according to the race and weight of the mice used.

It is ascertained in Table III that, 24 hours after having received the radioactive antigen, the control mice immunized with BAS only have a residual radioactivity very close to that of the nonimmunized control mice. On the contrary, the animals which have received with the antigen 50 $\mu g$ of the different hydrosoluble adjuvant preparations, purged the antigen substantially faster. This Table indicates the adjuvant action of all the hydrosoluble adjuvant agents according to the invention to be very effective. All of the mice which have received them at the same time as the antigen have higher circulant antibody rates (opsonins) than the control mice immunized without adjuvant, since the radioactive antigen is more quickly eliminated.

TABLE III

| Treatment | Residual radioactivity in the blood (%) | |
|---|---|---|
| Controls | 31.1* ± 6.9 | |
| BAS | 28.7 ± 12.9 | |
| BAS + 50 $\mu g$ "Substance C" | 14.7 ± 11.6 | p 0.05** |
| BAS + 50 $\mu g$ "Substance E1" | 12.1 ± 13.1 | p 0.05 |
| BAS + 50 $\mu g$ "Substance E2" | 11.7 + 10.9 | p 0.05 |

*Average representing the percentages obtained in 8 mice per group with standard deviation
**Signification degree according to Student test Demonstration of the inocuity of the substances according to the invention 1. Hyperreactivity to endotoxins It is well established that mycobacteria increase the susceptibility to the lethal effect of endotoxins. It has been admitted that this activity is related to the "cord factor" (E. Suter et Coll., Proc. Soc. Exp. Biol. Med. 1958, 99, 1967).

Groups of mice were sensitized 14 days (on day D - 14) before their being challenged with endotoxin, by intravenous injections, with BCG (Bacille Calmette Guerin) killed by phenol and in the form of whole cells, on the one hand, and with substances C1 and C2, on the other hand (doses of 300 $\mu g$ of the product tested suspended in saline).

Fourteen days later (on day D), all mice received an intravenous injection of an endotoxin preparation extracted from Salmonella enteriditis, strain Danysz.

As shown in Table IV, the $LD_{50}$ values of endotoxin are considerably higher with mice having been treated by substances according to the invention than with mice treated with BCG.

TABLE IV

| Treatment D-14 | Doses of endotoxyn ($\mu g$) | | | | $LD_{50}$ |
|---|---|---|---|---|---|
| | 1.5 | 5 | 15 | 50 | |
| BCG: 300 $\mu g$ i.v. | 6/8 | 7/8 | 8/8 | — | 1.5 |
| "Substance C1" 300 $\mu g$ i.v. | — | — | 0/8 | 0/8 | 50 |
| "Substance C2" 300 $\mu g$ i.v. | — | — | 0/8 | 0/8 | 50 |

2. Experimental polyarthritis of the rat

When complete Freund's adjuvant is injected in the footpad or hind leg of rats, there may be seen an articular oedema which is the most pronounced in the leg having received an injection with Freund's adjuvant but which is also visible in all the other articulations Modifications at the articular level which may be measured by the volume or the weight of the legs, are very substantial after 7 days and reach their maximum value 14 days after injection.

Groups (eight rats per group) were respectively injected into the hind legs, with the test substances in FIA (0.1 ml), with FIA alone, and with FIA containing BCG. All the animals were killed 17 days later and the weights of the bodies and the right legs measured. It will be noted that, at dosage shown in Table V, BCG causes a considerable increase of hind leg weight and a decrease of the rise of body-weight. On the contrary, animals having received substances shown in table V thereafter behave like normal controls having received only FIA.

TABLE V

|  |  | Body weight Jo | J14 | Right leg weight |
|---|---|---|---|---|
|  | Controls FIA | 250.4 | 284.6 | 2.938 |
| FIA + | BCG: 500 µg | 250.5 | 243.7 | 3.940 |
| FIA + | "Crude Substance C": 500 µg | 251.1 | 289.1 | 2.796 |
| FIA + | "Substance C": 500 µg | 251 | 276.6 | 2.725 |
| FIA + | "Substance D": 500 µg | 250.5 | 286.6 | 2.747 |
| FIA + | "Substance C1": 500 µg | 250.5 | 272 | 2.857 |
| FIA + | "Substance C2": 500 µg | 250.6 | 285.6 | 2.709 |

3. Hypertrophy of liver and spleen: comparison between BCG and agents of the invention It is well established that upon intravenous injection, mycobacteria cause a hypertrophy of liver and especially of the spleen which can be measured by an increase of the weight of said organs, 14 days after injection.

In these tests, the same hybrid mice have been used. The mice were injected with doses of 300 µg of the test substances (in solution in saline solute and, in some cases, in Bayol at 3 or 10). The mice were killed 14 days later.

The results shown in table VI hereunder correspond to the mean values for ten animals in each case of the body, spleen and liver weights respectively; as may be seen, the agents according to the invention do not cause any hypertrophy, contrary to BCG.

TABLE VI

|  | Body g | Spleen (mg) | Liver (mg) |
|---|---|---|---|
| Controls | 23 | 115 | 1.112 |
| BCG: 300 µg i.v. | 17.7 | 248 | 1.559 |
| "Substance C1": 300 µg i.v. | 20.7 | 118 | 1.147 |
| "Substance C2": 300 µg i.v. | 20 | 17.5 | 1.130 |

4. Sensitivity to histamine

It is well established that a surrenalectomized animal as well as an animal subjected to a previous treatment with *Bordetella pertussis* become highly sensitive to endotoxins and to histamine. Munoz and Suter (Proc. Soc. Exp. Biol. Med. 1963, 114, 211) have reported that, contrary to *B. pertussis*, BCG does not sensibilize to histamine and to passive anaphylactic shock. It has been assessed that said advantageous property has been preserved in the adjuvants according to the invention, as follows.

Increasing dosages of histamine are administered to groups of 8 mice belonging to "Swiss" race, having been treated seven days before (D-7) with dosages of 1 mg of the test agents as shown in Table VII hereunder, as well as to controls. All injections are intravenous. As may be seen in Table VII, mice having received the agent of the invention have substantially no increased sensitivity to histamine. This table shows the ratio of the number of mice which have died to the total number of mice in each group for each dosage of histamine.

TABLE VII

| Treatment | Sensitiveness to histamine Doses of histamine | | | |
|---|---|---|---|---|
|  | 4 mg | 8 mg | 16 mg | $LD_{50}$ |
| Normal Controls | 0/8 | 0/8 | 8/8 | 12.5 |
| "Substance C2" 1 mg i.v. | 0/8 | 2/8 | 8/8 | 10 |

5. Sensitivity to tuberculin

"Substance E1" and "Substance E2" do not produce in vitro blastic transformation of lymphocytes coming from human donors sensitive to tuberculin, in particular they are not capable of causing, like tuberculin, an increase of the incorporation of thymidin tritiated by lymphocytes in vitro.

Lymphocytes taken from tuberculino-sensitive donors are incubated in tubes according to the art of C. BONA, C. HEUCLIN and L. CHEDID (Enhancement of Mixed Human Lymphocyte Cultures by a Water-Soluble Adjuvant. Colloque CNRS, 1972). Each tube contains $10^6$ lymphocytes. There is added thereto, according to the tubes, either 10 µg of tuberculin, or 50 82 g of "Substance E1" or "Substance E2". The fourth day, 1 µ Ci of $H^3$ thymidin is added to each tube. The fifth day, the lymphocytes are removed and treated according to the above-mentioned art. There is shown in Table VIII that, in the tubes containing tuberculin, the incorporation of thymidin is considerably higher than in the control tubes (index: 5.57). On the contrary, in the tubes containing either "Substance E1" or "Substance E2", the incorporation of thymidin is not increased. These results demonstrate that the agents according to the invention do not contain tuberculin.

TABLE VIII

| Incubation | Average radioactivity (on 5 tubes) (c/mn) | Transformation index (radioactivity of treated lymphocytes/ radioactivity of control lymphocytes) |
|---|---|---|
| Controls | 8.791 | — |
| Tuberculin | 48.969 | 5.57 |
| "Substance E1" | 7.221 | 0.82 |
| "Substance E2" | 7.828 | 0.89 |

There are thus obtained adjuvants having a considerable activity while being free from objectionable secondary effects. The products may be used to increase efficiency of vaccines of bacterial or viral origin, especially with respect to weak immunogens. The products may be used, in particular, to enhance immunisation of host (humans or animals) against bacterial or viral infections, antigens of tumors, protozoan antigens, etc. They may also be used efficiently for the production of serums. They may be administered with antigen or vaccine of the kind aforesaid in pharmaceutically acceptable sterile injectable liquid vehicles, for instance sterile aqueous solutions-in-oil emulsions for instance water-in-hexadecane emulsions as well as oil free aqueous saline solutions.

For example, the substances according to the invention can be placed in suspension in the incomplete Freund's adjuvant or in a vehicle constituted by 8.5 parts of hexadecane, 1.5 parts of Arlacel or glycerol monoeleate and 10 parts of saline solution.

The administration may be effected as for a typical composition of the vaccine type, by intramuscular, intradermic or sub-cutaneous injection, as well as by scarification.

It is to be understood that the foregoing description has been given merely by way of an example, without any intent to limitation, the scope of the invention being defined by the appended claims.

We claim:

1. In the process for preparing a water-soluble immunological non-specific adjuvant which comprises
   treating an aqueous suspension of solvent-extracted delipidated whole cells of pathogenic and non-pathogenic Mycobacteria or Nocardia microorganisms with a muramidase to free the immunological non-specific adjuvant,
   separating the solid fraction from the mixture,
   recovering the aqueous portion containing aminoacids other than those of the peptidoglycan and the immunological non-specific adjuvant, the adjuvant having reduced sensitizing action to tuberculine.

2. The process of claim 1 wherein the muramidase is lysozyme.

3. The process of claim 1 which comprises the additional step of lyophilizing the aqueous fraction containing the immunological adjuvant, thereby obtaining a water-soluble product.

4. The process of claim 3 which comprises the additional step of taking up the dry lyophilized extract in an aqueous solution.

5. The process of claim 1 which comprises, for further purification, the additional step of incubating the aqueous medium of the immunological adjuvant with a proteolytic enzyme, whereby amino-acids are removed, and separating the more purified adjuvant.

6. The process of claim 5 wherein the enzyme is trypsin.

7. The process of claim 5 in which the aqueous medium is buffered at a pH from about 7.5 to about 8.2

8. The process of claim 1 which comprises the additional step of filtering the aqueous solution of the immunological adjuvant on a molecular sieve and recovering the filtrate containing the more purified aqueous solution containing the immunological adjuvant.

9. The process of claim 8 wherein the molecular sieve is of a polydextran column.

10. The process of claim 9 which comprises eluting with acetic acid several fractions from the column and collecting either the first or second fraction or the second and third fraction of the aqueous filtrate corresponding to the corresponding elution peak, said fractions containing the more purified immunological adjuvant.

11. The process of claim 10 in which the first or second fraction of the aqueous filtrate corresponding to the first or second elution peak of the filtrate, is recovered.

12. The process of claim 10 in which the second or third fraction of the aqueous filtrate corresponding to the second or third elution peak of the filtrate, is recovered.

13. The process of claim 1 in which the immunological non-specific adjuvant contains neutral sugars, amino sugars and amino acids.

14. In the process for preparing a water-soluble immunological non-specific adjuvant which comprises
   treating an aqueous suspension of solvent-extracted delipidated whole cells of pathogenic and non-pathogenic Mycobacteria or Nocardia microorganisms with a muramidase to free the immunological non-specific adjuvant,
   separating the solid fraction from the mixture,
   incubating the aqueous medium of the immunological adjuvant with a proteolytic enzyme, thereby removing amino acids, filtering the aqueous solution of the immunological adjuvant on a molecular sieve and recovering the filtrate containing the more purified aqueous solution containing the immunological adjuvant, the adjuvant having reduced sensitizing action to tuberculine.

* * * * *